(12) United States Patent
Albrecht

(10) Patent No.: US 10,126,381 B2
(45) Date of Patent: Nov. 13, 2018

(54) SHIELDING WITH INTEGRATED COOLING

(71) Applicant: Adam Albrecht, Nürnberg (DE)

(72) Inventor: Adam Albrecht, Nürnberg (DE)

(73) Assignee: Siemens Aktiengesellschaft, München (DE)

(*) Notice: Subject to any disclaimer, the term of this patent is extended or adjusted under 35 U.S.C. 154(b) by 1130 days.

(21) Appl. No.: 14/456,413

(22) Filed: Aug. 11, 2014

(65) Prior Publication Data

US 2015/0042342 A1    Feb. 12, 2015

(51) Int. Cl.
| | |
|---|---|
| *G01R 33/34* | (2006.01) |
| *A61B 5/055* | (2006.01) |
| *G01R 33/36* | (2006.01) |
| *H05K 7/20* | (2006.01) |
| *H05K 9/00* | (2006.01) |
| *H05K 1/02* | (2006.01) |
| *H05K 5/03* | (2006.01) |

(52) U.S. Cl.
CPC .......... *G01R 33/3403* (2013.01); *A61B 5/055* (2013.01); *G01R 33/36* (2013.01); *H05K 1/0272* (2013.01); *H05K 5/03* (2013.01); *H05K 7/20236* (2013.01); *H05K 9/0032* (2013.01)

(58) Field of Classification Search
CPC .... G01R 33/3403; G01R 33/36; A61B 5/055; H05K 7/20236; H05K 9/0032; H05K 1/0272; H05K 5/03
See application file for complete search history.

(56) References Cited

U.S. PATENT DOCUMENTS

| | | | |
|---|---|---|---|
| 6,052,284 A | 4/2000 | Suga et al. | |
| 7,285,851 B1 | 10/2007 | Cepeda-Rizo et al. | |
| 8,018,717 B2 * | 9/2011 | Corbeil | A61B 6/037 |
| | | | 165/104.33 |
| 8,338,794 B2 * | 12/2012 | Ladebeck | A61B 5/055 |
| | | | 250/370.11 |
| 8,441,260 B2 * | 5/2013 | Takegoshi | G01R 33/3621 |
| | | | 324/318 |
| 9,108,038 B2 * | 8/2015 | Brault | A61K 41/0004 |
| 9,151,814 B2 * | 10/2015 | Albrecht | G01R 33/3614 |
| 9,297,910 B2 * | 3/2016 | Liu | G01T 1/1618 |
| 9,404,982 B2 * | 8/2016 | Albrecht | G01R 33/28 |
| 2006/0291164 A1 | 12/2006 | Myers et al. | |
| 2011/0134610 A1 | 6/2011 | Baur et al. | |

FOREIGN PATENT DOCUMENTS

| | | |
|---|---|---|
| DE | 263161 A1 | 12/1988 |
| DE | 19734054 A1 | 2/1998 |
| EP | 1739746 A2 | 1/2007 |
| EP | 2330873 A1 | 6/2011 |

OTHER PUBLICATIONS

German Office Action dated Apr. 15, 2014 in corresponding German Patent Application No. DE 10 2013 215 843.2 with English translation.

* cited by examiner

*Primary Examiner* — Dixomara Vargas
(74) *Attorney, Agent, or Firm* — Lempia Summerfield Katz LLC

(57) ABSTRACT

An apparatus for cooling an electrical component includes a circuit board with the electrical component disposed on the circuit board. The apparatus includes a cover disposed on the circuit board. The cover and the circuit board form a closed cavity in which the electronic component is disposed. The cavity has a first opening for introduction of a fluid and a second opening for discharge of a fluid.

18 Claims, 2 Drawing Sheets

SHIELDING WITH INTEGRATED COOLING

This application claims the benefit of DE 102013215843.2, filed on Aug. 12, 2013, which is hereby incorporated by reference in its entirety.

FIELD

The disclosed embodiments relate to magnetic resonance tomography and cooling an electrical component.

BACKGROUND

In magnetic resonance measurements, the interaction of magnetic torques of atomic nuclei, the nuclear spins, is examined using an external magnetic field. The nuclear spins align themselves in the external magnetic field and process with a Larmor frequency. The Larmor frequency depends on the value of the magnetic torque of the atomic nucleus when excited by an external electromagnetic alternating field about the axis of orientation in the magnetic field. The atomic nuclei generate an electromagnetic alternating field with the Larmor frequency.

The external electromagnetic alternating field for exciting the nuclear spins is irradiated by one or more antennas into a sample or into a patient. One possible form of antenna is a body coil, which surrounds the patient or the sample. Local coils are however also used, which may be arranged directly on the patient or the sample. The electromagnetic alternating field generated by the atomic nuclei is also received by the antennas. The same antenna may receive the signal generated, or the nuclear spins may be excited using one type of antenna and the electromagnetic alternating field generated by the atomic nuclei is received by another type of antenna.

Both during the generation of the high-frequency electromagnetic alternating fields and also during the actuation of the gradient coils for the spatial resolution, powers in the range of kilowatts and voltages of several hundred or thousand volts are used. Hence the actuations also generate power losses of a comparable magnitude and benefit from efficient and high-capacity cooling. Also, because the measured high-frequency signals resulting from the excited nuclear spins are very weak, it is useful to ensure that electromagnetic interference fields generated by the actuations do not unintentionally bleed from the actuations and cause the measured signals to degrade.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the disclosed embodiments may provide an apparatus that provides effective and high-capacity cooling, simultaneously reduces stray radiation, and is easy to install.

An apparatus is described for cooling an electrical component. A magnetic resonance tomography system including the apparatus is also described. The apparatus has a circuit board with an electrical component disposed on the circuit board, and a cover disposed on the circuit board. The cover and the circuit board form a closed cavity in which the electronic component is disposed. The cavity has a first opening for the introduction of a fluid and a second opening for the discharge of a fluid.

The apparatus enables a fluid for cooling to be fed into the first opening, thereby filling the first cavity and flowing through the cavity, such that the fluid flows out of the second opening. The fluid flows around the component and absorbs heat, which is discharged with the outflowing fluid. The direct contact means that, with a suitable fluid, large volumes of heat may be discharged.

The magnetic resonance tomography system includes the inventive apparatus.

In one embodiment, a further cover is arranged on a surface of the circuit board lying opposite the first-named cover. The further cover and the circuit board form a further closed cavity.

With a further cavity, an electrical component may be cooled from both sides, if a fluid connection exists between the cavities or the further cover has separate openings for the fluid.

In one embodiment, the first-named cover and the further cover are in contact with the circuit board at opposing locations on the surfaces of the circuit board.

By mounting the circuit board between two covers, a larger force may be exerted onto the circuit board. The forces exerted by the covers cancel each other out on the opposing sides of the circuit board. As a result, a better seal between the circuit board and the covers may be achieved.

In one embodiment, the first-named cover and/or the further cover are made from an electrically conductive material.

An electrically conductive material shields against electromagnetic waves that are emitted by an electrical component. This may apply if two covers fully enclose both sides of the electrical component.

In one embodiment, the first-named cover and/or the further cover are made from several individual elements. For example, a cover may have a frame that forms side walls of the cavity, and a lid that closes the cavity opposite the circuit board.

This type of multipart embodiment of the cover is easier to manufacture, e.g., if the lid is made to be flat. The circuit board may be easily accessed if the lid is removed.

In one embodiment, an electrically conductive sealing mechanism (or seal) is disposed between the individual elements of the first-named cover and/or of the further cover.

The electrically conductive sealing mechanism creates a circumferential contact that, together with the conductive cover, provides (e.g., ensures) full shielding.

In one embodiment, the apparatus has an electrically conductive sealing mechanism (or seal) between the first-named cover and/or the further cover and the circuit board.

The electrically conductive sealing mechanism (or seal) between the circuit board and the first-named and/or further cover also provides (e.g., ensures) reliable shielding with respect to the circuit board.

In one embodiment, the first-named cover bounds a third cavity with the circuit board. The third cavity is delimited from the first cavity by a wall element.

With the third cavity, regions of the circuit board containing further components may be shielded without these components having to be sealed against contact with the fluid. In addition, it is not necessary to configure the third cavity to be fluid-proof, which simplifies the construction.

In one embodiment, a second electrical component is disposed on the wall element in the third cavity, and is in thermal contact with the wall element.

In this way, heat may be discharged from the second component via heat conduction through the wall element and released to the fluid.

In one embodiment, the circuit board is coated in the first cavity with an electrically insulating material such that a fluid in the first cavity does not come into contact with an electrically conductive contact of the circuit board or of the first-named component.

The electrically insulating material prevents electrical currents from unintentionally flowing between contacts through the fluid and interfering with the function of the components.

DETAILED DESCRIPTION

Figure 1:
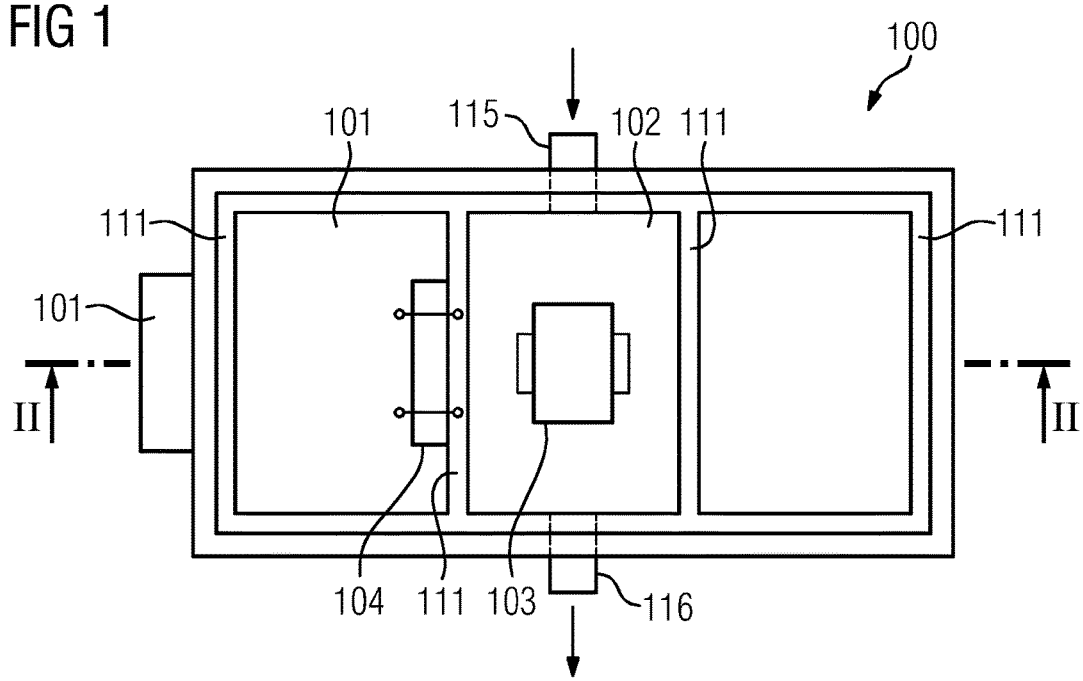
FIG. 1 shows a schematic, plan view of an apparatus in accordance with one embodiment.

FIG. 1 shows a plan view of an inventive apparatus 100, in which a lid 112 of the apparatus has been removed.

Figure 2:
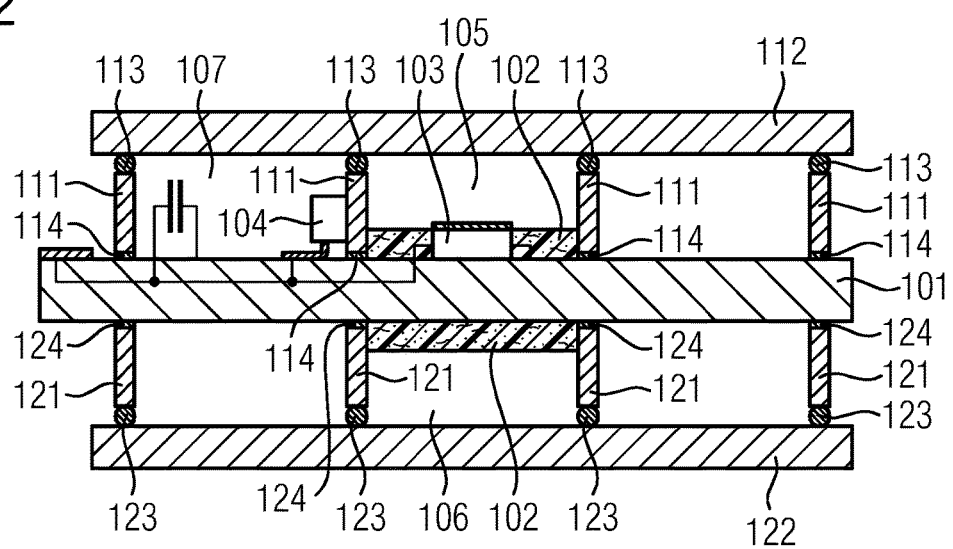
FIG. 2 shows a schematic, cross-sectional view of the apparatus of FIG. 1 along line II-II of FIG. 1.

FIG. 2 shows a schematic cross-section along a line II-II of FIG. 1. In FIG. 2, the lid 112 is disposed and illustrated at a location in accordance with one embodiment.

In the middle of the apparatus is a circuit board 101, which may have one, two or more layers including circuit paths. Disposed on the circuit board 101 are components 103, 104, which are electrically connected to circuit paths of the circuit board 101. A first component 103 has a large power loss and in operation warrants high cooling power, as well as a second component 105 with an average power loss and average cooling demands.

Arranged on the circuit board 101 are wall elements 111 that are constructed as part of a single-piece frame. As is apparent in FIGS. 1 and 2, the frame forms several regions that are each separated from one another by a wall 111. The wall 111 surrounds a region in each case on the outer circumference. Alternatively, several separate frames adjoining one another may be arranged on the circuit board 112, in order to separate the individual regions from one another. Alternatively, only a single frame may be provided, which merely surrounds a single region.

The frame or frames are in each case disposed in planar fashion on the side facing the circuit board 101 and opposite a lid 112, in order to provide as exact a fit as possible with the likewise planar circuit board 101 and the planar lid 112.

As is apparent in FIG. 2, a lid 112 is disposed on the walls 111, so that the walls 111 form closed cavities 105, 107 with the circuit board 101 and the lid 112. The first electrical component 103 is disposed on the circuit board 101 in the first cavity 105. In the third cavity 107 the second electrical component 104 is disposed on a wall 111 adjoining the first cavity 105.

The walls 111 or the frame 111 and the lid 112 are made of an electrically and thermally conductive material. This material may, for example, be aluminum or copper, but other metals or alloys with these properties may be used. For example, a resistance against a fluid used as a coolant may also be useful.

Disposed between lid 112 and walls 111 are sealing mechanisms (or seals) 113, which seal the respective cavities 105, 107 against one another in a fluid-proof manner. In the same way, sealing mechanisms 114 are disposed between the walls 111 and the circuit board 101, and seal the cavities 105, 107 in a fluid-proof manner. The cavity 105, through which, as explained below, a fluid flows, is hereby made fluid-proof with respect to the adjacent cavities.

In one embodiment, the sealing mechanisms 113, 114 are configured to be electrically conductive, so that, while providing the sealing, a conductive connection also exists between walls 111 and lid 112, or walls 111 and circuit board 101. In this way, the cavities 105, 107 each form a Faraday cage that restricts electromagnetic waves to the respective cavity 105, 106, 107 and prevents propagation into the surrounding area. Alternatively, the sealing mechanisms 113, 114 may not be conductive themselves, but a separate electrical connection is to be established using other conductive connecting elements such as screws, male multi-point connectors, contact springs or cables.

In the region which is open to the cavity 105, an electrically insulating material 102 is applied to the circuit board 101, and covers the entire surface of the circuit board belonging to the cavity 105 in a fluid-proof manner. The material 102 also covers all metal contacts of the first electrical component 103 provided with an electrical potential and thereby insulates the first electrical component 103 from a fluid provided in the cavity 105. The electrically insulating material 102 may, for example, be an epoxy resin poured into the cavity 105, after the frame 101 has been disposed on the circuit board.

As is apparent from FIG. 1, the cavity 105 additionally has two openings 115, 116 on walls 111, through which an exchange of fluid is possible with the interior of the cavity 105. Thus, for example, a fluid may be introduced as a coolant into the cavity 105 through the fluid feed 115, and flows around the first electrical component 104 and, in this way, effectively cools the first electrical component 104. The heated fluid may then be discharged again by way of the second opening 116 as a fluid outflow. The fluid also cools the walls 111 of the cavity 105 and thus the second electrical component 104, which in the third cavity 107 is in thermal contact with the wall 111 on the opposing side of the wall 111. Because the transport of heat is degraded because of heat resistance of the wall 111, the cooling power is reduced with respect to the electrical component 103. Depending on the electrical circuit and construction of the second electrical component, the second electrical component 104 is electrically insulated with respect to the wall 111 using an insulating mechanism.

Illustrated in the embodiment in FIG. 2 on a side of the circuit board 101 opposing the frame 111 is another frame 121 or walls 121 and a lid 122, which, as already described, likewise bounds cavities 106 with the circuit board 101. No other electrical components are illustrated in FIG. 2, but electrical components may also be arranged in the second cavity 106 and on the adjacent wall 112. The second cavity 106 also has an electrically insulating material 102 on the surface of the circuit board 101. Otherwise, the cavities 106 bounded by the frame 121 and the lid 122 correspond in terms of their properties with the previously described cavities 105, 107. For example, the cavities 106 are provided with comparable sealing mechanisms (or seals) 123, 124.

For optimum cooling, in one embodiment, the circuit board 101 may have openings, through which a fluid flows from the first cavity 105 into the second cavity 106 and back. As a result, cooling of the first component 103 also takes place from the other side of the circuit board 101. The second cavity 106 may have a separate fluid inflow and fluid outflow or otherwise for the first cavity 105 to be supplied with fluid via the openings in the circuit board 101. In one embodiment, fluid openings may be in the lids 112, 122 instead of in the walls 111, 121.

In one embodiment, water, e.g., distilled water, is provided as a fluid, because water has a particularly high thermal capacity and does not damage the environment.

Other fluids such as oils or synthetic liquids may also be used, e.g., liquids resistant to high voltages. The electrically insulating material 102 may then be dispensed with, for example.

The walls 111 and 121 are in one embodiment in each case arranged adjacently on opposing sides of the circuit board 101. In this way a larger force may be exerted on the walls, without distorting the circuit board. As a result, a good seal may be achieved between circuit board 101 and the walls 111, 121. Furthermore, the opposing cavities, such as the first cavity 105 and the second cavity 106, form a common shielding of the circuit board 101 outward through the conducting walls 111, 121 and the lids 112, 122. By being bolted to each other, the frames 111, 121 and lids 112, 122 may, for example, clamp the circuit board 101 between the frames and lids or may be pressed from the outside against the circuit board 101 via additional retaining elements.

In one embodiment, one or more cavities 105, 106 may be provided only on one side of the circuit board 101. In this case, the circuit board 101 itself shields the interior of the cavity 105, 106 by metal layers. The circuit board is pressed firmly enough against the frame 111 via a suitable construction, for example, via a support frame.

Figure 3:
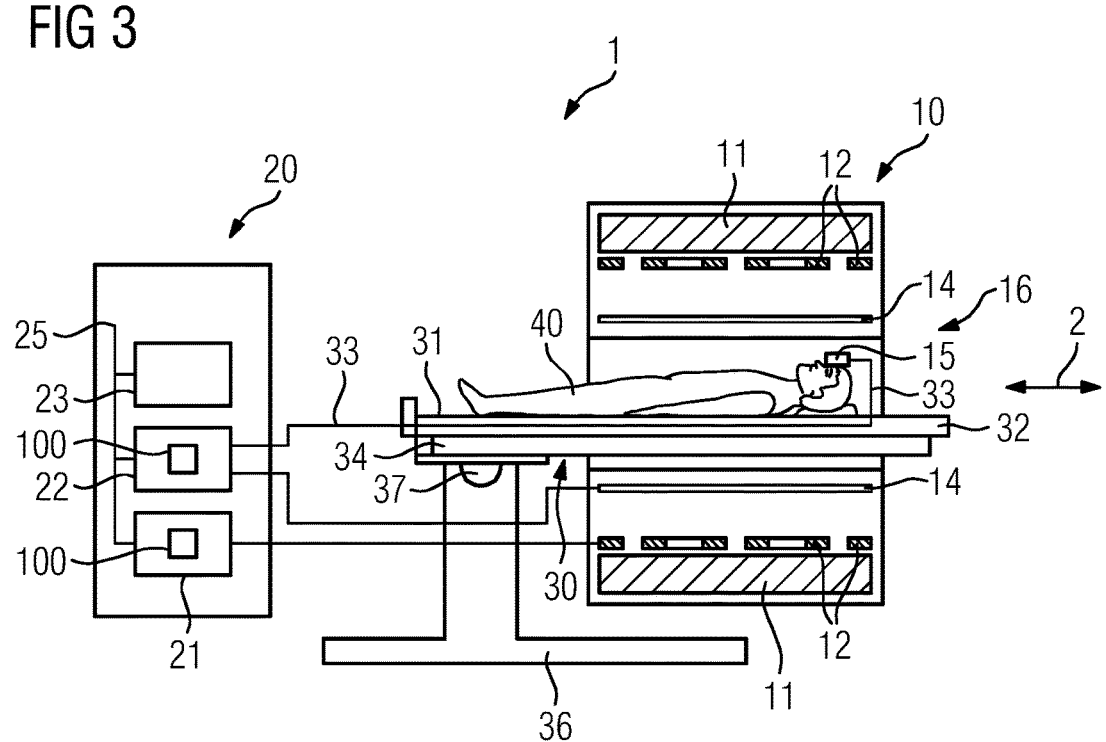
FIG. 3 shows a schematic illustration of a magnetic resonance tomography system in accordance with one embodiment.

FIG. 3 schematically shows a magnetic resonance tomography system 1, in which inventive apparatuses 100 are used.

The magnetic resonance tomography system 1 has a magnet unit 10 with a field magnet 11 that generates a static magnetic field $B_0$ to align nuclear spins of samples or of a patient 40 in a sample volume. The sample volume is arranged in a passthrough or opening 16 that extends in a longitudinal direction 2 through the magnet unit 10. The field magnet 11 may be a superconducting magnet that may provide magnetic fields having a magnetic flux density of up to 3 T or higher. For lower field strengths, permanent magnets or electromagnets with normal-conducting coils may also be used.

Furthermore, the magnet unit 10 has gradient coils 12 configured to overlay the magnetic field $B_0$ with variable magnetic fields in three spatial directions for the spatial differentiation of the captured imaging regions in the sample volume. The gradient coils 12 may be coils made of normal-conducting wires that may generate fields orthogonal to one another in the sample volume.

The magnet unit 10 furthermore has a body coil 14 and local coils 15. Both the body coil 14 and the local coil 15 are also characterized as antennas 14, 15 in the following description, because both are suitable for emitting a high-frequency electromagnetic alternating field into their surrounding area. The body coil 14 is used among other things as a transmit coil if as homogeneous as possible an electromagnetic excitation field is to be generated across a large volume.

A magnetic resonance signal excited by the electromagnetic alternating field of the body coil 14 or of the local coils 15 and by the static magnetic field $B_0$ in the patient may be received either by the transmit coils 15 or by the separate body coil 14, which may receive signals from the entire examination region.

A control unit 20 supplies the magnet unit 10 with the various signals for the gradient coils 12 and the body coil 14 or the local coils 15 and evaluates the signals received.

Thus the control unit 20 has a gradient control 21 configured to provide the gradient coils 12 with variable currents via feed lines. The variable currents provide the desired gradient fields in the sample volume on a temporally coordinated basis. The gradient control 21, to actuate the gradient coils 12, generates signals with a voltage of over a thousand volts and an output of kilowatts at working frequencies in the kilohertz range and multiple harmonic components thereof. It is hence useful for the gradient control to have an apparatus 100 in order to provide sufficient cooling and good shielding combined with simple construction.

Furthermore, the control unit 20 has a transceiver device 22 configured to generate, for antenna 14, 15, a high-frequency pulse with a predetermined time characteristic, amplitude, phase and spectral power distribution to excite a magnetic resonance of the nuclear spins in the patient 40. In this case pulse powers in the kilowatt range may be achieved. It is therefore useful for the transceiver device 22 also to have an apparatus 100 in order to provide sufficient cooling and good shielding combined with simple construction.

The transceiver unit 22 is furthermore configured to evaluate, in terms of amplitude and phase, high-frequency signals received from the body coil 14 or one or more transmit coils 15 and fed to the transceiver unit 22 via a signal line 33. This relates to high-frequency signals that emit nuclear spins in the patient 40 in response to the excitation by a high-frequency pulse in the magnetic field $B_0$ or in a magnetic field resulting from an overlay of $B_0$ and gradient fields.

Furthermore, the control unit 20 has a controller 23 configured to undertake the temporal coordination of the activities of the gradient control 21 and the transmit devices 22 for the purpose of image capture via magnetic resonance tomography. To this end the controller 23 is connected to the other units 21, 22 via a signal bus 25 and exchanges signals with the other units 21, 22. The controller 23 is configured to accept and process signals from the patient 40 evaluated by the transceiver unit 22 or to define and temporally coordinate pulse and signal shapes for the gradient control 21 and the transceiver unit 22.

The patient 40 is disposed on a patient couch 30. The patient couch 30 is used in magnetic resonance tomography. The patient couch 30 has a first support 36 disposed under a first end 31 of the patient couch 30. So that the support 36 may hold the patient couch 30 in a horizontal position, the support 36 may have a foot that extends along the patient couch 30. To move the patient couch 30, the foot may also have a mechanism for movement, such as castors. Apart from the support 36 on the first end 31, no structural element is disposed between the floor and the patient couch, so that the patient couch may be introduced as far as the first end 31 into the opening 16 of the field magnet 11. FIG. 1 shows linear rail systems 34 that movably connect the support 36 to the patient couch 30, so that the patient couch may travel in the longitudinal direction 2. To this end the linear rail system has a drive 37 that enables an operator or the controller 23 to move the patient couch 30 in the longitudinal direction 2 in a controlled manner. As a result, regions of the body of the patient may be examined that have a larger extent than the sample volume in the opening 16.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for cooling an electrical component, the apparatus comprising:
a circuit board on which the electrical component is disposed; and
a cover disposed on the circuit board;
wherein the cover and the circuit board form a closed cavity in which the electronic component is located; and
wherein the closed cavity has a first opening for introducing a fluid and a second opening for discharging the fluid, wherein the first and second openings are formed in walls of the closed cavity, the first and second openings having a smaller cross-section relative to a direction of flow than the walls and the closed cavity.

2. The apparatus of claim 1, further comprising a further cover disposed on a surface of the circuit board opposing the first-named cover, wherein the further cover and the circuit board form a further closed cavity.

3. The apparatus of claim 2, wherein the first-named cover and the further cover are in contact with the circuit board at opposing locations on surfaces of the circuit board.

4. The apparatus of claim 2, wherein the first-named cover, the further cover, or both the first-named cover and the further cover are made of an electrically conductive material.

5. The apparatus of claim 2, wherein the first-named cover, the further cover, or both the first-named cover and the further cover are formed from several individual elements.

6. The apparatus of claim 5, wherein an electrically conductive seal is disposed between the individual elements of the first-named cover, the further cover, or both the first-named cover and the further cover.

7. The apparatus of claim 5, wherein electrically conductive seals are disposed between the circuit board and the first-named cover, the further cover, or both the first-named cover and the further cover.

8. The apparatus of claim 1, wherein the first-named cover bounds a further cavity with the circuit board, the further cavity being delimited from the first-named cavity by a wall element.

9. The apparatus of claim 8, wherein a further electrical component is disposed on the wall element in the further cavity and is in thermal contact with the wall element.

10. The apparatus of claim 1, wherein the circuit board is coated in the cavity with an electrically insulating material such that a fluid in the cavity does not come into contact with an electrically conductive contact of the circuit board or of the electrical component.

11. The apparatus of claim 1, further comprising an electrically insulating material covering the electrical component in the closed cavity, wherein the fluid contacts the electrically insulating material in the cavity.

12. A magnetic resonance tomography system comprising an electrical unit, the electrical unit comprising an apparatus for cooling the electrical unit, the apparatus comprising:
a circuit board on which the electrical unit is arranged; and
a cover disposed on the circuit board;
wherein the cover and the circuit board form a closed cavity in which the electronic component is located;
wherein the closed cavity has a first opening for introducing a fluid and a second opening for discharging the fluid; and
an electrically insulating material covering the electrical component in the closed cavity, wherein the fluid contacts the electrically insulating material in the cavity.

13. The magnetic resonance tomography system of claim 12, wherein the apparatus further comprises a further cover disposed on a surface of the circuit board opposing the first-named cover, wherein the further cover and the circuit board form a further closed cavity.

14. The magnetic resonance tomography system of claim 13, wherein the first-named cover and the further cover are in contact with the circuit board at opposing locations on surfaces of the circuit board.

15. The magnetic resonance tomography system of claim 13, wherein the first-named cover, the further cover, or both the first-named cover and the further cover are made of an electrically conductive material.

16. The magnetic resonance tomography system of claim 12, wherein the first and second openings are formed in walls of the closed cavity, the first and second openings having a smaller cross-section relative to a direction of flow than the walls and the closed cavity.

17. The magnetic resonance tomography system of claim 12, wherein the electrical component is within the closed cavity.

18. An apparatus for cooling an electrical component, the apparatus comprising:
a circuit board on which the electrical component is disposed; and
a cover disposed on the circuit board;
wherein the cover and the circuit board form a closed cavity in which the electronic component is located, wherein the electrical component is within the closed cavity; and
wherein the closed cavity has a first opening for introducing a fluid and a second opening for discharging the fluid.

* * * * *

UNITED STATES PATENT AND TRADEMARK OFFICE
CERTIFICATE OF CORRECTION

PATENT NO. : 10,126,381 B2
APPLICATION NO. : 14/456413
DATED : November 13, 2018
INVENTOR(S) : Adam Albrecht Page 1 of 1

It is certified that error appears in the above-identified patent and that said Letters Patent is hereby corrected as shown below:

On the Title Page

Please add: "Foreign Application Priority Data: DE 10 2013 215 843.2 filed August 12, 2013"

Signed and Sealed this
Ninth Day of April, 2019

Andrei Iancu
*Director of the United States Patent and Trademark Office*